United States Patent [19]
Daniell et al.

[11] Patent Number: 5,932,479
[45] Date of Patent: *Aug. 3, 1999

[54] GENETIC ENGINEERING OF PLANT CHLOROPLASTS

[75] Inventors: Henry Daniell, Moscow, Id.; Bruce A. McFadden, Pullman, Wash.

[73] Assignee: Auburn University, Auburn University, Ala.

[ * ] Notice: This patent is subject to a terminal disclaimer.

[21] Appl. No.: 08/591,407

[22] Filed: Jan. 25, 1996

Related U.S. Application Data

[63] Continuation of application No. 08/215,020, Mar. 18, 1994, abandoned, which is a continuation of application No. 07/249,616, Sep. 26, 1988, abandoned.

[51] Int. Cl.⁶ ............... C12N 15/29; C12N 15/82; C12N 5/04
[52] U.S. Cl. ............ 435/468; 435/320.1; 435/418; 435/419; 536/23.6; 536/24.1; 800/278; 800/287; 800/288; 800/298; 800/300; 800/307; 800/308; 800/312; 800/320; 800/320.1; 800/320.2; 800/320.3; 800/322
[58] Field of Search ............ 435/172.3, 240.4, 435/320.1, 419, 418, 468; 800/205, DIG. 26, DIG. 55–58, 278, 287, 288, 298, 300, 307, 308, 312, 320, 320.1, 320.2, 320.3, 322

[56] References Cited

FOREIGN PATENT DOCUMENTS 0251654  1/1988  European Pat. Off. .

OTHER PUBLICATIONS

Sugita et al. Plant Mol. Biol. 32:315–326, 1996.
Herrera–Estrella et al. Nature 310: 115–120, 1984.
Link, G. 1991. pp. 365–394 In: Cell Culture and Somatic Cell Genetics of Plants, vol. 7B., Academic Press, Inc.
Daniell, H. 1993. pp. 536–556. Foreign Gene Expression in Chloroplasts of Higher Plants Mediated by Tungsten Particle Bombardment, Academic Press, Inc.
Daniell et al. 1990. Proc. Natl. Acad. Sci. USA 87: 88–92.
boynton et al. 1988. Science 240: 1534–1538.
DeBlock et al. 1985. EMBO J 4(6):1367–1372.

*Primary Examiner*—David T. Fox
*Attorney, Agent, or Firm*—Weiser and Associates, P.C.

[57] ABSTRACT

Methods for the transformation of etioplasts and of chloroplasts are disclosed. One method comprises incubating isolated etioplasts with a chelating agent to bind metal ions on which chloroplast nucleases are dependent and incubating the resultant nuclease-inactivated etioplasts with foreign DNA. By an alternative method of transforming chloroplasts, foreign DNA comprising expression cassettes are coated on metal particles and inserted by high-velocity impact into plant cells. For transformation into a plant chloroplast, DNA molecules containing an expression cassette includes a DNA fragment containing appropriate control sequences. The expression cassette may also be flanked by chloroplast DNA which facilitates stable integration of the gene(s) of interest into the recipient chloroplast genome. It is desirable to include within the expression cassette a selectable marker gene that encodes a selectable phenotype which allows for the identification of the cells expressing the introduced gene. Transformed chloroplasts, transformed etioplasts, transformed cells and their progeny, and plants are disclosed. Other aspects of the invention are described.

42 Claims, 4 Drawing Sheets

GENETIC ENGINEERING OF PLANT CHLOROPLASTS

This application is a continuation of application Ser. No. 08/215,020, filed Mar. 18, 1994, now abandoned, which is a continuation of application Ser. No. 07/249,616, filed Sep. 26, 1988, now abandoned.

TECHNICAL FIELD OF THE INVENTION

The present invention is directed to plants and the genetic engineering thereof. More particularly, the present invention is directed to the transformation of plant chloroplasts with foreign DNA.

BACKGROUND OF THE INVENTION

Most strategies for gene transfer in plants involve the introduction of foreign DNA into protoplasts to enable its integration into the nuclear genome (1–3). However, many of the economically important gene products (e.g., the protein conferring atrazine resistance) either are chloroplast encoded or, if they are nucleus encoded, are functional within the chloroplasts (e.g., enol-pyruvylshikimate-phosphate synthase, which confers resistance to glyphosate) (4) or mitochondria (e.g., aryl acylamidase, which confers resistance to propanil) (5, 6). Furthermore, the 1000-fold higher copy number of chloroplast genes relative to nuclear genes (7–9) makes feasible the introduction of multiple copies of foreign genes into plant cells, should the foreign genes become stably integrated into the chloroplast genome.

To obtain gene transfer into chloroplasts, the isolation of intact organelles capable of efficient uptake, transcription, and translation of foreign DNA is essential. As a first step towards achieving this goal, Daniell and Rebeiz isolated plastids from dark-growth cucumber cotyledons (etioplasts) capable of synthesis of protocholorophyllide (10) and chlorophyll (11–13) at extremely high rates. Also, etioplasts that had been loaded with prothylakoid proteins by treatment of etiolated cucumber cotyledons with hormones (14) converted prothylakoids into macrograna when illuminated in a cofactor-enriched medium (15). Daniell and colleagues also demonstrated the development of electron transport coupled to photophosphorylation in concordance with the synthesis of required polypeptides in isolated etioplasts (16, 17). Finally, they also observed linear biosynthesis of pigment and translation of endogenous messages for 8 hr. (18). These observations collectively establish that etioplasts of cucumber cotyledons are both metabolically very active and unusually stable in their capacity for protein synthesis, marking them as exceptional targets for gene incorporation and expression.

SUMMARY OF THE INVENTION

The present invention provides a method for transforming plants with foreign DNA by introducing foreign DNA into chloroplasts. Thus, in one embodiment, the present invention provides a chloroplast from a plant comprising foreign DNA. In another embodiment, the present invention is directed to a method of providing for the uptake of foreign DNA into a chloroplast comprising incubating said chloroplast with a chelating agent that chelates metal ions employed by chloroplast nucleases to provide nuclease-inactivated chloroplasts; and incubating said nuclease-inactivated chloroplasts with foreign DNA whereby said foreign DNA is taken up within the chloroplast membrane.

BRIEF DESCRIPTION OF THE DRAWINGS

FIG. 3.(A) Autoradiograph reflecting immunoprecipitation of the small subunit (SSU) of RuBisCO from [$^{35}$S] methionine-labeled etioplasts. Sonic extracts (100 µl, each containing 850 µg of plastid protein) of EDTA-washed etioplasts were treated with preimmune serum and subsequently immunoprecipitated with specific antiserum to the small subunit of *A. nidulans* RuBisCO, after incubation of etioplasts minus pCS75 (lane 2) or plus supercoiled pCS75 (lane 3). Lane 1 reflects the treatment with preimmune serum of sonic extracts of EDTA-washed etioplasts that had been incubated with pCS75. Lane 4 represents [$^{14}$C] methylated protein standards, with molecular masses shown in kDa. (B) Expression of CAT with pUC9-CM in etioplasts that had been treated for different durations with 10 mM EDTA. CAT was assayed by thin-layer chromatography of [$^{14}$C] chloramphenicol and its faster-migrating acetylated products. Lanes were as follows: 1, purified *E. coli* CAT (Pharmacia); 2, negative control, minus etioplast extract; 3–7, EDTA treatment for 0.5, 10, 20 and 30 min., respectively. Except as noted, all incubation mixtures contained 20 µg of supercoiled pUC9-CM and 50 µg of calf thymus carrier DNA and etioplasts containing 850 µg of protein. (C) Expression of CAT with pUC9-CM: Effects of gene dosage, ribonuclease, and protease. Lanes reflect the following: 1–5, etioplasts that had been incubated with 0, 2, 4, 6, and 10 µg of supercoiled pUC9-CM, respectively. Etioplasts in lanes 6–8 had been incubated with 10 µg of supercoiled pUC9-CM. Each incubation mixture contained 50 µg of calf thymus carrier DNA and etioplasts (900 µg of protein). Etioplasts were treated with (lane 6) or without (lane 7) thermolysin (100 µg/ml) for 30 min. at 4° C. after coupled transcription-translation; the reaction was stopped by the addition of 10 mM EDTA and the etioplasts were washed once in the isolation medium prior to breakage. Alternatively, etioplasts were incubated in the presence of ribonuclease (500 µg/ml) during transcription-translation (lane 8).

DETAILED DESCRIPTION OF THE INVENTION

Figure 1:
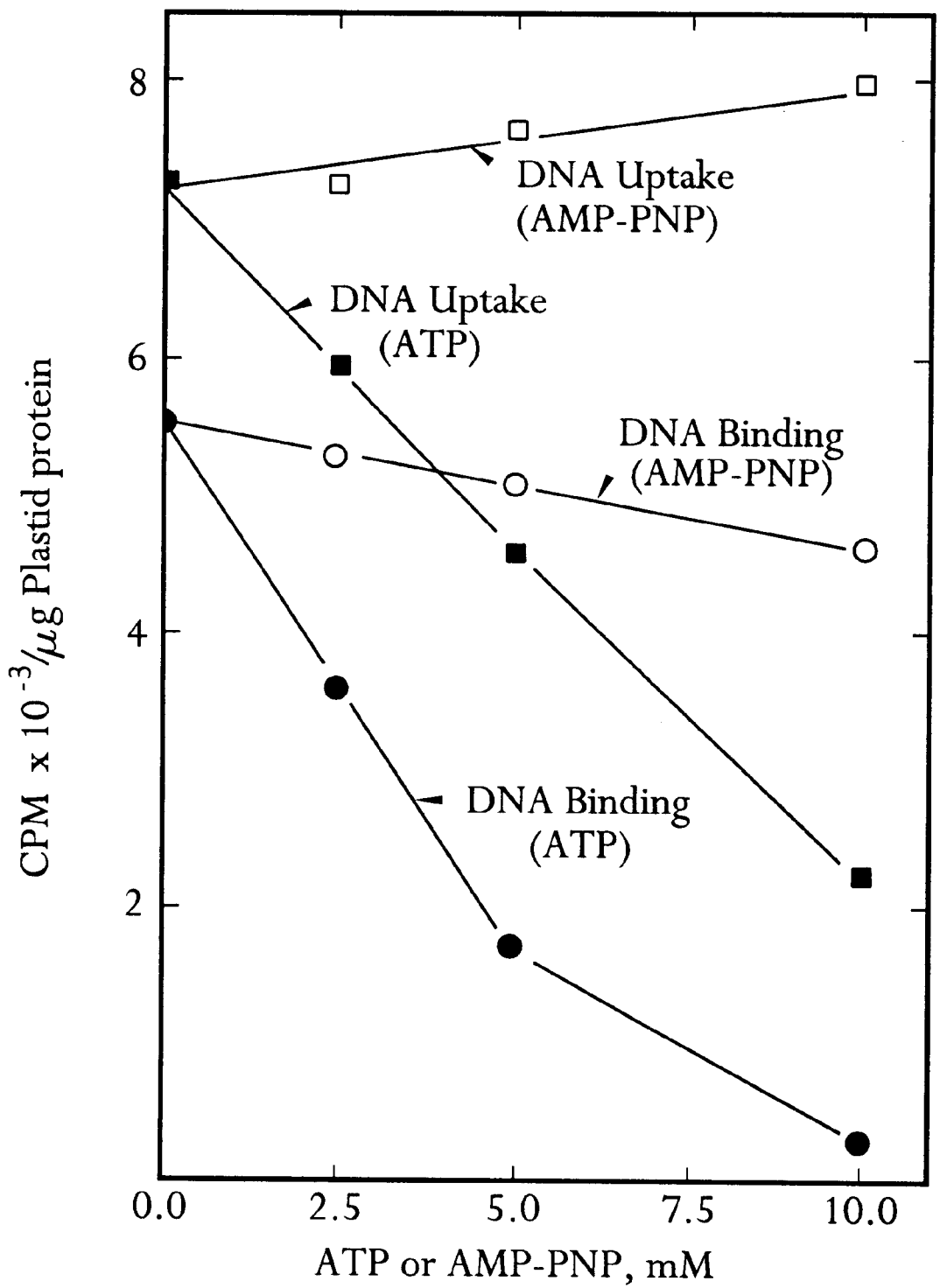
FIG. 1. Effect of ATP or its analog adenyl-5'-yl imidodiphosphate (AMP-PNP) on the uptake or binding of the labeled donor DNA by etioplasts. Etioplasts were incubated with the indicated concentrations of ATP or its analog (pH 7.0) in the presence of nick-translated $^{32}$P-labeled pCS75 for 2 hr in the light at 27° C.

In addition to the techniques described below, the practice of the present invention will employ conventional techniques of molecular biology, microbiology, recombinant DNA technology, and plant science, all of which is within the skill of the art. Such techniques are explained fully in the literature. See, e.g., Maniatis et al., Molecular Cloning: A Laboratory Manual (1982); DNA Cloning: Volumes I and II (D. N. Glover ed. 1985); Oligonucleotide Synthesis (M. J. Gait ed. 1984); Nucleic Acid Hybridization (B. D. Hames & S. J. Higgins eds. 1985); Transcription and Translation (B. D. Hames & S. J. Higgins eds. 1984); Animal Cell Culture (R. I. Freshney ed. 1986); Plant Cell Culture (R. A. Dixon ed. 1985); Propagation of Higher Plants Through Tissue Culture (K. W. Hughes et al. eds. 1978); Cell Culture and Somatic Cell Genetics of Plants (I. K. Vasil ed. 1984); Fraley et al. (1986) CRC Critical Reviews in Plant Sciences 4:1 (hereinafter Plant Sciences); Biotechnology in Agricultural Chemistry: ACS Symposium Series 334 (LeBaron et al. eds. 1987).

In describing the present invention, the following terminology will be used in accordance with the definitions below.

A "replicon" is any genetic element (e.g., plasmid, cosmid, chromosome, virus, etc.) that behaves as an autonomous unit of DNA replication in vivo; i.e., capable of replication under its own control within a cell.

A "vector" is a replicon, such as a plasmid, cosmid, or bacteriophage, to which another DNA segment may be attached so as to bring about replication of the attached segment.

A "DNA molecule" refers to the polymeric form of deoxyribonucleotides (adenine, guanine, thyine, or cytosine) in either single- or double-stranded form. When in the double-stranded form, the molecule will usually be in its normal, double-stranded helix. The term "DNA molecule" is not limited to any particular tertiary form of DNA. Thus, the term includes double-stranded DNA found, inter alia, in linear DNA molecules, viruses, plasmids and chromosomes. When discussing the structure of particular double-stranded DNA molecules, sequences may be described herein according to the normal convention of giving only the sequence in the 5' to 3' direction (left to right) along the nontranscribed (anti-sense) strand of DNA (i.e, the strand having a sequence homologous to the mRNA). If both strands are shown, the anti-sense strand win be on top.

A DNA "coding sequence" is a DNA sequence which is transcribed and translated into a polypeptide in vivo when placed under the control of appropriate regulatory sequences. The boundaries of the coding sequence are determined by the start codon at the 5' terminus and a translation stop codon at the 3' terminus. Examples of coding sequences include cDNA reverse transcribed from eukaryotic mRNA, genomic DNA sequences from eukaryotic cells, and synthetic DNA sequences.

A cell which has been "transformed" by an exogenous DNA sequence is a cell into which the exogenous DNA has been introduced. The exogenous DNA may be integrated (covalently linked) to chromosomal DNA making up the genome of the cell, or it may remain extrachromosomal. "Stably" integrated DNA sequences are those which are inherited through chromosome replication by daughter cells or organisms (accounting for loss by Mendelian segregation). This stability is exhibited by the ability to establish cell lines or clones comprised of a population containing the exogenous DNA.

A "clone" or "cell line" is a population of cells descended from a single cell or common ancestor by mitosis and is capable of stable growth in vitro for many generations.

A composition of a first type of matter (e.g., a DNA molecule containing a coding region) is "substantially free" of a second type of matter (e.g., DNA molecules which do not contain a coding region) if the composition is comprised of less than about 10% (weight/weight) of the second type of matter relative to the sum of the first and second types of matter. Preferably, the composition contains less than about 5% of the second type of matter, most preferably less than about 1%.

A cell organelle, such as a chloroplast, has been "transformed" by an exogenous (foreign) DNA sequence if exogenous for foreign DNA has been introduced inside the organelle membrane. The foreign DNA may be integrated (covalently linked) into chloroplast DNA making up the genome of the organelle, or it may remain unintegrated (e.g., by including a chloroplast origin of replication). "Stably" integrated DNA sequences are those which are inherited through organelle replication, thereby transferring new organelles through the cytoplasm to daughter cells.

The term "chloroplast" includes all developmental stages of a chloroplast, such as proplastids, etioplasts, and mature chloroplasts. In the practice of the present invention, it is preferred to transform etioplasts.

"Plant" refers to any higher or lower plant, particularly dicots and monocots. In particular, the present invention is directed to important dicotyledons such as peas, lentils, watermelon, sunflower, soybeans, and cucumbers, as well as important monocotyledons, such as wheat, corn, barley, and rice. Chloroplasts from all lower and higher plants are very similar in properties, and the present invention is therefore directed to all such organisms and their chloroplasts.

In the practice of the present invention, foreign DNA is provided for transformation into a plant chloroplast. Foreign or exogenous DNA refers to any DNA which is not found within the chloroplast in nature. Thus, foreign DNA can encompass a wide variety of DNA molecules. Particularly referred are DNA molecules containing an expression cassette; i.e., a DNA construct comprising a coding sequence and appropriate control sequences (e.g., promoter and appropriately matched transcription termination sequence) to provide for the proper expression of the coding sequence in the chloroplast. Typically, the expression cassette is flanked by convenient restriction sites to facilitate cloning. In a preferred embodiment, the foreign DNA used for transformation comprises an expression cassette flanked by chloroplast DNA to facilitate the stable integration of the expression cassette into the chloroplast genome by homologous recombination.

In constructing the above expression cassettes, one will employ a promoter operable in the chloroplast of interest. Typically, chloroplast promoters will be employed, although many procaryotic (e.g., bacterial) promoters are functional in chloroplasts. Important coding sequences which can be used in the above expression cassettes include genes for herbicide resistance, such as the atrazine resistance gene psIIB (Cheung et al., 1986, Proc. VII Intl. Cong. on Photosynthesis, pp. 210–494) and the glyphosate resistance gene ES-3-P synthetase (Comai, U.S. Pat. No. 4,535,060). Additional coding sequence which may be of interest include mutants of the gene for ribulose bisphosphate carboxylase/oxygenase (RuBisCO), which may increase catalytic activity and thereby elevate the level of photosynthesis and plant growth.

It is usually desirable to include with the expression cassette a selectable marker gene which encodes a selectable phenotype; i.e., a phenotype of a cell or organism which allows for the identification or selection of cells expressing the selectable marker gene. Well-known marker genes include, but are not limited to, the gene for chloramphenicol acetyltransferase (CAT), neomycin phosphotransferase (neo$^R$), neomycin phosphotransferase II (npt-II), nopaline synthase (NOS), dihydrofolate reductase (mtx$^R$), hypoxanthine phosphoribosyl transferase (hpt), and thymidine kinase (tk).

The expression cassette is constructed so that the coding sequence is loaded within the cassette along with the appropriate control sequences, the positioning and orientation of the coding sequence with respect to the control sequences being such that the coding sequence can be transcribed under the control of the regulatory sequences (i.e., by RNA polymerase, which attaches to the DNA molecule at the control sequences) in the host chloroplast transformed by the expression cassette. It is possible to assemble to the expression cassette prior to inserting it into a cloning vector. Alternatively, an expression cassette can be constructed by cloning the coding sequence directly into an expression vector already containing the appropriate regulatory sequences and the restriction site downstream from the promoter.

It is particularly preferred to use, as foreign DNA for chloroplast transformation, DNA molecules containing an expression cassette using a chloroplast promoter.

Examples of such promoters include the psbA promoter, the rbcL promoter, and the atpB promoter. See, e.g., Gruissem et al. (1985) EMBO J 4:3375–3383. An example of such foreign DNA is expression vector pHD407, which comprises the psbA promoter inserted as a BamHI-HindIII fragment into the pKK232-8 vector (Brosius, 1984, Gene 27:151, commercially available from Pharmacia) at the appropriate restriction site upstream from the promoter-less CAT coding sequence.

According to one embodiment of the present invention, foreign DNA, such as DNA molecules containing the expression cassettes described above, are used to transform isolated chloroplasts by direct uptake. This method takes advantage of the fact that the chloroplast membrane is believed to be porous, thus allowing for the entry of exogenous DNA into the organelle. It has been found to be critical to pretreat isolated chloroplasts with a metal chelating agent, such as EDTA, to bind the metal ions on which the chloroplast nucleases are dependent. In the absence of pretreatment with a metal chelating agent, chloroplast nucleases are available to degrade foreign DNA as it enters through the chloroplast membrane. The particular chelating agent and the protocol (e.g., time, temperature, concentration, etc.) for pretreatment are not critical within wide parameters. Numerous chelating agents and pretreatment protocols are within the skill of the art. All that is required is that the protocol be such that the chloroplasts survive and that a sufficient inhibition of nuclease activity occurs to permit a high level of transformation to occur relative to untreated chloroplasts (e.g., at least 10-fold). The preferred chelating agent is EDTA, and a preferred protocol is described below.

As an alternative method of transforming chloroplasts, foreign DNA comprising expression cassettes as described above can be coated on metal particles and inserted by high-velocity impact on cultured cells or callus tissue of intact plant cells. It is believed that a certain proportion of the foreign DNA will find its way into chloroplasts and be expressed there. See, e.g., Klein et al. (1987) Nature 327:70.

When isolated chloroplasts are transformed directly, it will be necessary to reintroduce the chloroplast into plant cells. Large numbers of chloroplasts can be taken up by plant protoplasts, particularly when the protoplasts have been treated with PEG (polyethylene glycol). See, e.g., Carlson (1973) Proc. Natl. Acad. Sci. USA 70:598–602; Bonnett et al. (1974) Planta 120:71–79; Bonnett (1976) Planta 131:229–233.

Once transformed plant cells have been produced, it is usually desirable to grow the cells into callus or a cell line in suspension. Techniques for regenerating callus and for producing cell lines are known in the art. Transformed cells can also be induced to undergo organogenesis. Alternatively, the transformed cells can be used to regenerate plants from tissue culture. Various techniques of callus tissue culture, organ culture, and plant regeneration are known. The selection of the appropriate method for a plant species is within the skill of the art.

Set forth below are specific examples of the present invention which are intended for illustrative purposes only. These examples are not intended to limit the present invention in any manner. The references cited herein, as well as Daniell & McFadden (1987) Proc. Natl. Acad. Sci. USA 84:6349–6353, are incorporated by reference herein.

MATERIALS AND METHODS

Cucumber seeds (*Cucumis sativus Linnaeus*) were germinated in moist Vermiculite at 32° C. for 3 days in the dark. *E. coli* strain HB101 harboring the plasmid pCS75 was a gift from F. R. Tabita (University of Texas at Austin) and was grown in TYE medium at 37° C. (19). The plasmid pUC9-CM (incorrectly printed as pUC9M in ref. 20), a derivative of pUC9 with an insert of a nucleotide 1192–2480 Hae II-Sau3A fragment from pACYC 184 containing the coding sequence of the CAT gene with its promoter, was a gift from G. An (Washington State University, Pullman). Plasmids pCS75 and pUC9-CM were isolated as described (21). All solutions used for treatment of cotyledons and isolation or treatment of etioplasts were sterile and manipulations were carried out under aseptic conditions. All pH adjustments were done at 25° C. and centrifugations were carried out at 4° C.

Four to eight batches (50 each batch) of 3-day germinated cotyledons were excised with hypocotyl hooks and each batch was incubated in the dark at 32° C. in 10 ml of 0.5 mM kinetin (prepared as a 15 mM stock, solubilized with NaOH) and 2 mM gibberellic acid in large (10-cm) deep Petri dishes for 20 hr. After the hooks had been removed, each batch was hand homogenized with 10 pestle strokes in a prechilled mortar and pestle in 20 ml of the isolation medium, which consisted of 0.5 M sucrose, 15 mM Hepes, 30 mM 2-{[tris (hydroxymethyl)methyl]amino} ethanesulfonic acid (Tes), 1 mM MgCl$_2$, 1 mM EDTA, 5 mM cysteine, 2 mM dithiothreitol, and 2% bovine serum albumin at a final pH of 7.7. The homogenate was passed through four layers of autoclaved chilled cheesecloth. The homogenate was then centrifuged at 200×g for 3 min. at 4° C. and the plastids were sedimented by centrifuging the resultant supernatant for 7 min. at 1500×g. Suspensions of etioplasts from different batches were pooled and purified by layering on 35 ml of 0.6 M sucrose prepared in the homogenization medium and centrifuging at 500×g for 15 min (22). The plastids, after treatment in the presence or absence of EDTA (as described in the next section), were suspended in an ice-cold medium A, which consisted of 0.5 M sucrose, 15 mM Hepes, 30 mM Tes, 40 mM NAD, 2.5 mM EDTA, and 1 % bovine serum albumin with a final pH of 7.7. This medium was derived from the previously described translation medium for cucumber etioplasts (18), after deletion of ATP and metallic ions, which we found to inhibit DNA uptake.

EDTA-washed etioplasts were prepared according to Daniell and Rebeiz (13) by suspending etioplasts pelleted from the 0.6 M sucrose homogenization buffer in an EDTA wash buffer, pH 7.7, which consisted of 0.5 M sucrose, 15 mM Hepes, and 30 mM Tes containing 10 mM EDTA. After 10 min. of incubation at 0–4° C. in the dark, the suspended etioplasts were pelleted at 1500×g for 7 min. and resuspended in medium A as described in the preceding section.

Etioplasts, untreated or treated with EDTA, were incubated at 3.0 ml of medium A containing 1 μg of [$^{32}$P]DNA per ml, which had been labeled by nick-translation of pCS75 using [α-$^{32}$P]dCTP and DNA polymerase 1 (23). Incubations were carried out at 27° C. for different durations with cool white fluorescent light [intensity: 30 μE-m$^{-2}$s$^{-1}$; 1 E (einstein)=1 ml of photons] on a reciprocating shaker operated at 60 oscillations per min. in a water bath. Binding, uptake and breakdown of DNA were measured as described previously (23).

EDTA-treated etioplasts were incubated in a water bath in resuspension medium A without or with plasmid DNA (50 μg/ml) at 27° C. for 2 hr. with cool white fluorescent light (30 μE-m$^{-2}$s$^{-1}$) on a reciprocating shaker operated at 60 oscillations per min. At the end of the incubation, the plastids were pelleted at 1500×g for 7 min. and the incubation medium was discarded. Etioplasts were washed thoroughly with ice-cold medium B (0.5 M sucrose/15 mM Hepes/30 mM Tes, pH 7.7) and were resuspended in transcription-translation medium, which contains the following components at a final pH of 8.2: 0.4 M sucrose [RNase-, DNase-, and protease-free (Schwartz/Mann)], 50 mM Tris acetate, 60 mM potassium acetate, 11 mM ammonium acetate, 14 mM magnesium acetate, 20 mM ATP, 0.5 mM GTP, 0.5 mM CTP, 0.5 mM UTP, 0.5 mM cAMP, 10 mM phosphoenolpyruvate, type III pyruvate kinase (Sigma, 6.4 units/ml of final incubation mixture); *E. coli* tRNA (0.125 μg/ml), 19 amino acids (0.2 mM each), 0.14 mM pyridoxine-HCl, 0.1 mM FAD, 0.1 mM NADP, 0.06 mM p-aminobenzoic acid, 1.6 mM dithiothreitol, 1% polyethylene glycol 6000, and 20 μCi 1 (1 Ci=37 GBq) of [$^{35}$S] methionine per 100-μl reaction mixture. Each component was stored independently as a 10× stock solution at −20° C. Storage of combined reaction mixture at −20° C. resulted in rapid loss of transcription-translation. Incubations were carried out for 2 hr. at 27° C. At the end of each incubation, the plastids were centrifuged, washed once with ice-cold medium B, and finally frozen in liquid nitrogen in suitable aliquots.

β-Lactamase was assayed by a spectrophotometric method (21) in which the β-lactam ring of nitrocefin ($\lambda_{max}$=390 nm) is hydrolyzed to the ring-opened product ($\lambda_{max}$=490 nm). Immunoprecipitation of small subunits of RuBisCO with antiserum to the *A. nidulans* protein (raised in rabbits by Jose Torres-Ruiz of our laboratory) was done essentially described previously (21). CAT was assayed in etioplast sonic extracts as reported in ref. 24 except that the amount of [$^{14}$C] chloramphenicol was decreased to 50 nCi per sample.

RESULTS

Preliminary experiments on incubation of etioplasts with nick-translated $^{32}$P-labeled pCS75 (3.8×10$^8$ cpm/μg of plasmid) showed a linear increase in uptake or binding of DNA at 27° C. for at least 120 min. Therefore, all incubations of DNA with etioplasts were carried out for 2 hr. DNase treatment of etioplasts ensured that the high (Table 1) and continuing uptake of DNA observed was due to intact organelles, confirming earlier results (15) with an organelle fraction isolated identically. The rate of uptake of [$^{32}$P] pCS75 by etioplasts in the light, 0.86×10$^4$ cpm/μg of protein, was comparable to a value of 1.35×10$^4$ cpm/μg of protein calculated for "permeaplasts" of *A. nidulans* when [$^{32}$P]-pBR322 of approximately identical specific radioactivity were used (22). Permeaplasts are cells with partially digested cell wall obtained by treatment of cells with lysozyme and EDTA (22). Etioplasts that had been subjected to 10-min incubation at 0–4° C. in the dark in the sucrose/Hepes/Tes buffer lacking EDTA showed only 3% of as much uptake DNA as was observed with EDTA-washed etioplasts after 2 hr of incubation with nick-translated [$^{32}$P]pCS75 (Table 1). On the other hand, 42% as much binding of DNA as had been observed with EDTA-washed etioplasts was observed with etioplasts washed in the absence of EDTA under identical conditions of incubation. The presence or absence of light did not affect DNA uptake, binding, or breakdown in etioplasts washed in the presence or absence of EDTA (Table 1). Cations such as calcium or magnesium ions significantly inhibited DNA uptake (86%) in EDTA-washed etioplasts enhanced binding (23–200%) and breakdown (163–235%) DNA (Table 1).

It has been previously suggested that the calcium-dependent breakdown of donor DNA, reflected in the perchloric

TABLE 1

Characterization of DNA uptake, binding, and breakdown by etioplasts

| | cpm × 10$^{-4}$/mg plastid protein (%) | | |
|---|---|---|---|
| Experimental conditions | Uptake | Binding | Breakdown |
| Untreated etioplasts | | | |
| Control, light | 28 (100) | 215 (100) | 297 (100) |
| Control, dark | 28 (100) | 194 (90) | 282 (95) |
| + gramicidin | 30 (107) | 187 (87) | 325 (100) |
| + gramicidin + NH$_4$Cl | 30 (108) | 203 (95) | 337 (110) |
| + valinomycin | 29 (103) | 204 (95) | 337 (108) |
| + ATP | 7 (25) | 22 (10) | 297 (114) |
| EDTA-washed etioplasts | | | |
| Control, light | 856 (100) | 465 (100) | 154 (100) |
| Control, dark | 788 (92) | 456 (90) | 139 (90) |
| + magnesium acetate | 124 (14) | 570 (123) | 516 (335) |
| + MgCl$_2$ | 124 (14) | 681 (146) | 470 (305) |
| + CaCl$_2$ | 119 (14) | 1392 (300) | 404 (263) |
| + gramicidin | 822 (96) | 471 (101) | 156 (263) |
| + gramicidin + NH$_4$Cl | 813 (95) | 470 (101) | 160 (104) |
| + valinomycin | 805 (94) | 446 (96) | 167 (108) |
| + ATP | 197 (23) | 51 (11) | 152 (99) |

Etioplasts were incubated in medium A with 1 μg of nick translated $^{32}$P-labeled pCS75 under various conditions. The additional components were added at the following concentrations: gramicidin, 10 μM; NH$_4$Cl, 5 mM: valinomycin, 10 μM; ATP 10 mM; magnesium acetate, 20 mM; MgCl$_2$, 20 mM; and CaCl$_2$, 20 mM acid-soluble fraction, may be an essential requirement for transformation of *Bacillus subtilis* (25–27). However, in studies of yeast protoplasts, binding of plasmid DNA was not accompanied by its degradation (28). We have demonstrated recently that DNA uptake in permeaplasts of *A. nidulans* is unrelated to the breakdown of donor DNA (22). In the present work on etioplasts, cations inhibited DNA uptake but enhanced breakdown (Table 1), suggesting that the two processes may be unrelated in this case also.

Protonmotive force, which consists of a membrane potential (Δψ) and proton gradient (ΔpH), has been shown to be the driving force for DNA uptake in the transformation of some bacteria (29). Therefore, the effect of various reagents that inhibit ATP synthesis or uncouple photophosphorylation from photoelectron transport was investigated. Gramicidin forms an aqueous transmembrane channel through which protons pass slowly but does not inhibit electron transfer even at very high concentrations; gramicidin inhibits phosphorylation by abolishing $\Delta\psi$ without having a major effect upon the transmembrane $\Delta$pH (30). To achieve total uncoupling by abolishing both $\Delta\psi$ and $\Delta$pH, we used the "uncoupler couple" $NH_4Cl$ plus gramicidin. Neither gramicidin alone nor gramicidin together with $NH_4Cl$ had any effect on DNA uptake, binding, or breakdown by etioplasts (Table 1). In *B. subtilis,* valinomycin, a dissipator of the $\Delta\psi$ component of the protonmotive force, inhibited DNA binding (29), but this compound had no effect on DNA uptake or binding by etioplasts (Table 1). In *B. subtilis,* DNA uptake or binding is an active process driven by protonmotive force (29), whereas in yeast protoplasts (28), cyanobacterial permeaplasts (22), or etioplasts (Table 1) each is a passive process.

Both DNA uptake and DNA binding were severely inhibited in etioplasts by ATP, but the breakdown of DNA was essentially unaffected (Table 1). The effect was almost certainly due to the hydrolysis of ATP, because the nonhydrolyzable (or very poorly hydrolyzable) ATP analog adenyl-5'-yl imidodiphosphate did not inhibit uptake or binding of DNA (FIG. 1). The striking inhibition of DNA binding (and binding-dependent uptake) by ATP is reminiscent of the effect of ATP on the same phenomena observed with permeaplasts of *A. nidulans* (22). Because this ATP analog is noninhibitory, we conclude that externally added ATP may phosphorylate one or more etioplast membrane components that are involved in DNA binding.

Figure 2:
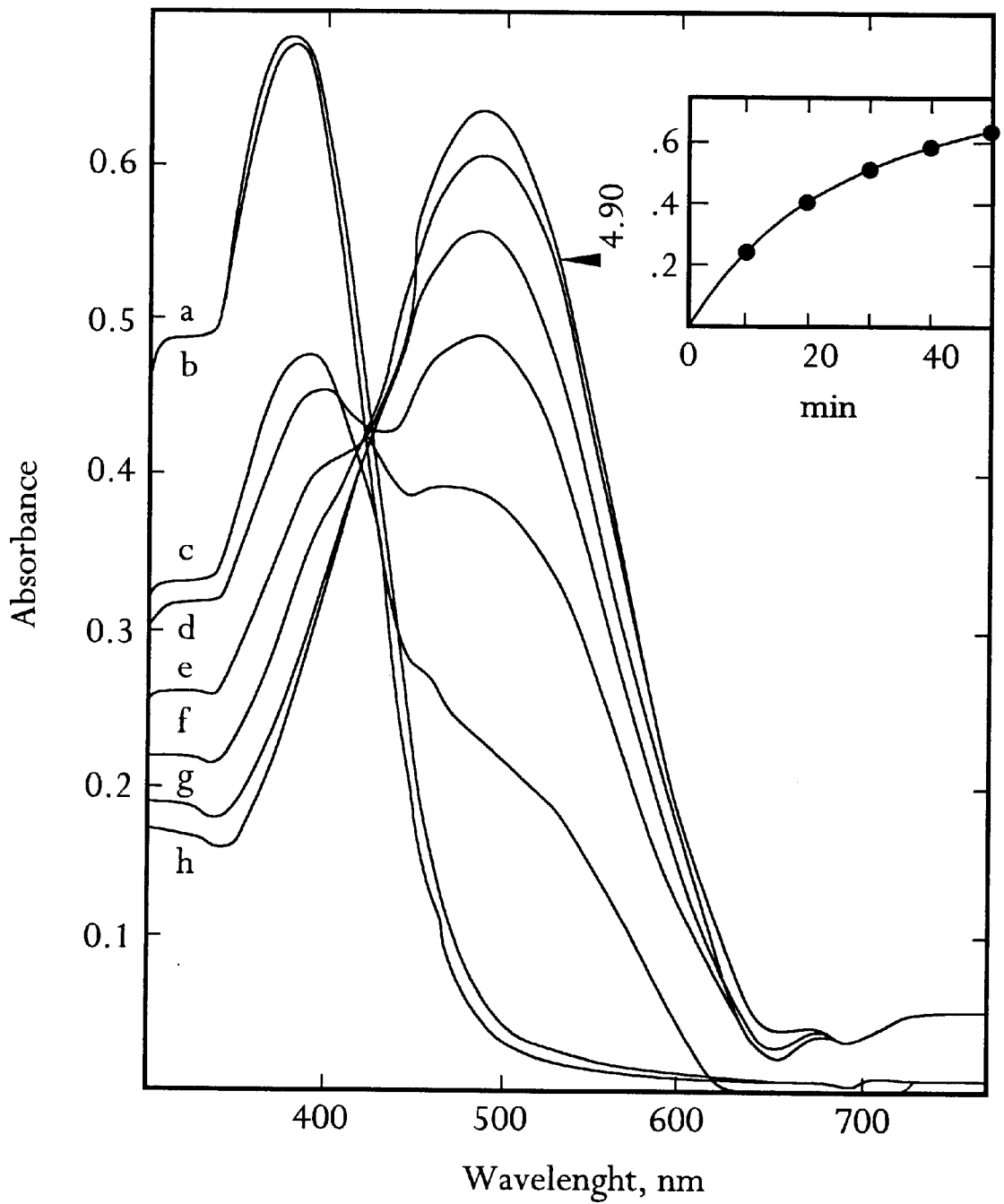
FIG. 2. Assay of β-lactamase based on the hydrolysis of the β-lactam ring of nitrocefin in sonic extracts of etioplasts. The spectral shift ($\lambda_{max}$=390 nm to $\lambda_{max}$=490 nm) after hydrolysis catalyzed by β-lactamase establishes that the reaction was almost complete in a 60-min incubation at 20° C. The traces represent nitrocefin alone (a) or incubated with etioplast sonic extract (b) or with sonic extract from etioplasts that had been incubated with supercoiled pCS75 and assayed for 10, 20, 30, 40, 50, or 60 min (c–h, respectively). Spectral scan times were 30 sec. (Inset) Change of $A_{490}$ with time, reflecting data from traces c–g.

The introduction and expression of foreign DNA measured by assaying β-lactamase encoded by the plasmid pCS75, using a spectrophotometric method in which a spectral shift from 390 nm to 490 nm accompanies hydrolysis of the β-lactam ring of nitrocefin (23). Whereas sonic extracts of etioplasts (incubated in the absence of DNA did not hydrolyze nitrocefin, those incubated with DNA hydrolyzed nitrocefin (FIG. 2). The initial rate of nitrocefin hydrolysis by transformed etioplasts with 0.12 $A_{490}$ unit/min per mg of protein, may be compared with a value of 0.4 obtained for pBR322 transformants of permeaplasts of *A. nidulans* (23). In transformed higher plant protoplasts, nitrocefin hydrolysis was extremely slow and could be detected only after an 18-hr incubation (31).

In these experiments, special precautions were taken to minimize the possibility that bacterial contamination of etioplasts could account for these results. To address this question, bacteria were enumerated at 30° C. and 37° in etioplast fractions (with or without EDTA treatment) incubated in the presence or absence of pCS75. Bacterial contamination was estimated in terms of the ratio of bacterial protein to etioplast protein. The high ratios of etioplast bacterial protein (data not shown) established that bacterial contamination was minimal. Moreover, ampicillin-resistant bacterial could not be detected after plating etioplast fractions on LB medium containing ampicillin. In this connection, it should also be pointed out that in *B. subtilis* and *E. coli,* DNA uptake and binding are quenched by EDTA and uncouplers (29), in contrast to our results with etioplasts (Table 1). Moreover, with those bacteria, $Ca^{2+}$-dependent breakdown of donor DNA may be required for transformation (25–27).

Figure 3A:
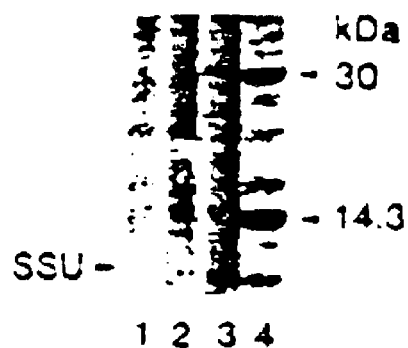
FIGS. 3A–3C.

The plasmid pCS75 carries the genes for the large and small subunits of RuBisCO from *A. nidulans.* Immunoprecipitation of the translation products with antiserum to the small subunit of RuBisCO from *A. nidulans* suggested the presence of labeled 12-kDa small subunits in etioplasts incubated with pCS75 (FIG. 3A), a molecular mass that is in accord with that for the small subunit of RuBisCO from *A. nidulans* (19). To check for contamination of etioplasts by cytoplasmic messages, experiments were carried out in cotyledons labeled with [$^{35}$S] methionine in vivo. Etioplasts preincubated with pCS75 showed a translation product 2 kDa smaller than that of cucumber encoded by its nuclear genome (data not shown). Our immunoblots further revealed that cucumber small subunit strongly crossreacts with the small subunit of RuBisCO from *Chromatium vinosum* but not with that from *A. nidulans.* It is known that newly synthesized stromal proteins of low molecular mass are almost completely degraded in chloroplasts in the presence of ATP (32, 33). The imported RuBisCO small subunit is also destroyed rapidly by proteolysis when conditions for assembly with the large subunit are limiting (34). Therefore, studies of the expression of *A. nidulans* small subunit (FIG. 3A) were not pursued.

Figure 3B:
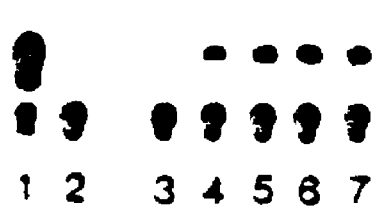
Figure 3C:
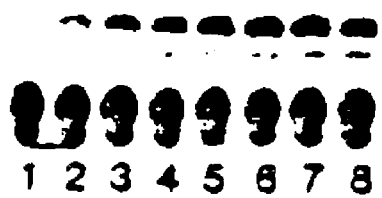

Etioplasts treated with EDTA (10 mM) for various times showed that 10 min. was optimal for the expression of CAT (FIG. 3B). The background activity observed in etioplasts in the absence of DNA (FIG. 3C, lane 1) could have been due to a low level of endogenous acetylase activity found to be present in all plant species tested (35). A progressive increase in the expression of CAT was observed with an increase in the concentration of pUC9-CM in the DNA uptake medium (FIG. 3C). Furthermore, treatment of etioplasts with ribonuclease during incubation in the transcription-translation reaction mixture or with thermnolysin after coupled transcription-translation did not affect the expression of CAT (FIG. 3C) or incorporation of [$^{35}$S] methionine (data not shown). These results with thermolysin and ribonuclease confirm our conclusion that etioplasts are indeed intact during translation.

Figure 4:
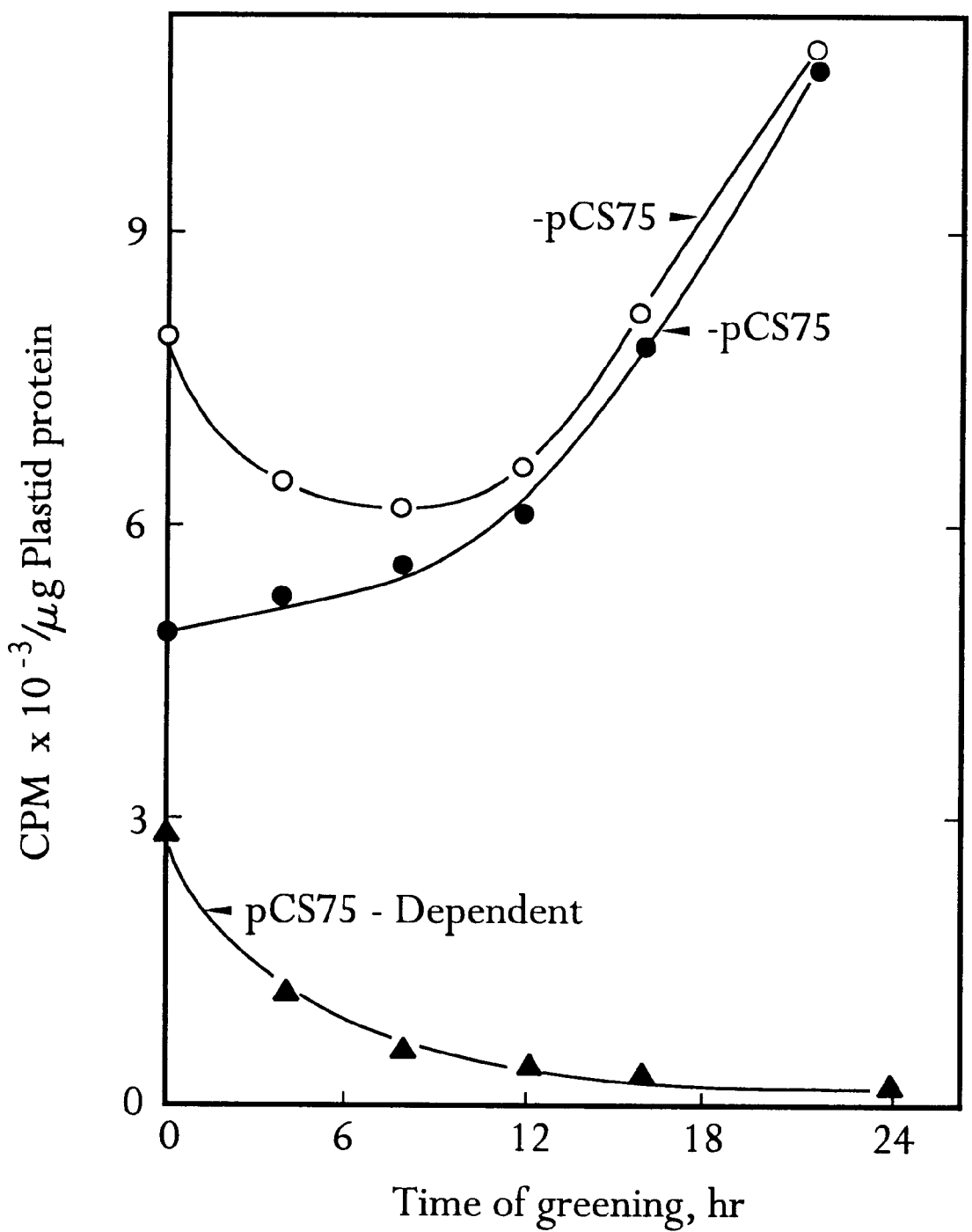
FIG. 4. Translation competence of etioplasts during greening. Incorporation of [$^{35}$S] methionine into the hot trichloroacetic-acid insoluble fraction after incubation of cucumber etioplasts isolated at different stages of greening: with (○) or without (●) the plasmid pCS75. Also shown is DNA-dependent translation (▲), which is the difference between translation with and without plasmid.

All of the present studies (FIGS. 1–3) were conducted etioplasts isolated at zero-time greening. In organello translation of endogenous mRNA in ethiochloroplasts isolated from cucumber at different stages of greening showed a continuous increase as greening progressed (FIG. 4). In contrast, DNA dependent incorporation of [$^{35}$S] methionine decreased dramatically as the tissue matured, and only 5% of transcription/translation activity towards foreign DNA remained after 24 hr. of greening. It seems likely that the overall enhancement in translation of 60% observed in pCS75-treated etioplasts (FIG. 4) was due to protection of endogenous mRNA by incorporated plasmid. In this connection, carrier DNA has been used in addition to plasmid DNA to increase translation by plant protoplasts that were subject to electroporation (35, 36).

1. Nester, E. W., Gordon, M. P., Amasino, R. M. & Yanofsky, M. F. (1984) *Annu.Rev. Plans Physiol.* 35, 387–13.
2. Fromm, M., Taylor, L. P. & Walbot, V. (1985) *Proc. Natl. Acad. Sci. USA* 82, 5824–5828.
3. Crossway, A., Hauptli, H., Houck, C. M., Irvine, J. M., Oakes, J. V. & Peram, L. A. (1986) *BioTechniques* 4, 320–334.
4. Della-Cioppa, G., Bauer, C. S., Klein, B. K., Shah, D. M., Fraley, R. T. & Kishore, G. M. (1986) *Proc. Natl. Acad. Sci. USA* 83,6873–6877.
5. Daniell, H., Sarojini, G., Kumarachinnayan, P. & Kulandaivelu, G. (1981) *Weed Res.* 21, 171–177.
6. Gaynor, J. J. & Still, C. C. (1983) *Plant Physiol.* 72, 80–85.
7. Bennett, J. & Radcliffe, C. (1975) *FEBS Lett.* 56, 222–225.
8. Coruzzi, G., Broglie, R., Edwards, C. & Chua, N. H. (1984) *EMBO J.* 3, 1671–1679.

9. Coen, D. M., Bedbrook, J. R., Bogarad, L. & Rich, A. (1977) *Proc. Natl. Acad. Sci. USA* 74, 5487–5491.
10. Daniell, H. & Rebeiz, C. A. (1982) *Biochem. Biophys. Res. Commun.* 104, 837–843.
11. Daniell, H. & Rebeiz, C. A. (1982) *Biochem. Biophys. Res. Commun.* 106, 466–470.
12. Rebeiz, C. A., Daniell, H. & Mattheis, J. R. (1982) *Biotechnol. Bioeng.* 12, 413–439.
13. Daniel, H. & Rebeiz, C. A. (1984) *Biotechnol. Bioeng.* 26, 481–487.
14. Daniell, H. & Rebeiz, C. A. (1986) in *Regulation of Chloroplast Differentiation,* Plant Biology Series, eds. Akoyunogiou, G. & Senger, H. (Liss, New York), pp. 63–70.
15. Rebeiz, C. A., Montazer-Zouhoor, A. & Daniell, H. (1984) in *Chloroplast Development: Structure, Function and Regulation of the Photosynthetic Apparatus,* eds. Ohad, I. & Klein, S. (Weizmann Sci. Presse, Jerusalem), pp. 225–235.
16. Daniell, H., Ramanujam, P., Krishnan, M., Gnanam, A. & Rebeiz, C. A. (1983) *Biochem. Biophys. Res. Commun.* 111, 740–749.
17. Daniell, H. & Sarojini, G. (1984) in *Advances in Photosynthesis Research,* ed. Sybesma, C. (Junk, The Hague, The Netherlands), Vol. 4, pp. 689–692.
18. Daniell, H., Krishnan, M., uma Bai, U. & Gnanam, A. (1986) *Biochem.* Biophys. Res. Commun. 135, 248–255.
19. Tabita, F. R. & Small, C. L. (1985) *Proc. Natl. Acad. Sci. USA* 82, 6100–6103.
20. Buckley, K. J. & Hayashi, M. (1986) *Ml. Gen. Genet.* 204, 120–125.
21. Daniell, H., Sarojini, G. & McFadden, B. A. (1986) *Proc. Natl. Acad. Sci. USA* 83, 2546–2550.
22. Pardo, A. D., Chereskin, B. M., Castelfranco, P. A., Franceschi, V. R. & Wezelman, B. E. (1980) *Plant Physiol.* 65, 956–960.
23. Daniell, H. & McFadden, B. A. (1986) *Ml. Gen. Genet.* 204, 243–248.
24. Gormon, C. M., Moffat, L. F. & Howard, B. H. (1982) *Ml. Cell. Biol.* 2, 1044–1051.
25. Joenje, H. & Venema, G. (1975) *J. Bacteriol.* 122, 25–33.
26. Mulder, J. A. & Venema, G. (1982) *J. Bacteriol.* 150, 260–268.
27. Smith, H., Wiersma, K., Venema, G. & Bron, S. (1984) *J. Bacteriol.* 157, 733–738.
28. Brzobohary, B. & Kovac, L. (1985) *FEBS Lett.* 183, 211–214.
29. van Neiuwenhoven, M. H., Hellingwerf, K. J., Venema, G. & Konings, W. N. (1982) *J. Bacteriol.* 151, 771–776.
30. McCarty, R. E. (1980) *Methods Enzymol.* 69, 719–728.
31. Lurquin, P. F. & Kleinhofs, A. (1982) *Biochem. Biophys. Res. Commun* 107, 286–293.
32. Malek, L., Bogorad, L., Ayers, A. R. & Goldberg, A. L. (1984) *FEBS Lett.* 166, 253–257.
33. Liu, X. & Jagendorf, A. T. (1984) *FEBS Lett.* 166,k 248–252.
34. Schmidt, G. W. & Mishkind, M. L. (1983) *Proc. Natl. Acad. Sci. USA* 80, 2632–2636.
35. Ou-Lee, T. M., Turgeon, R. & Wu, R. (1986) *Proc. Natl. Acad. Sci. USA* 83, 6815–6819.
36. Ow, D. W., Wood, K. V., Deluca, M., de Weet, J. R., Helinski, D. R. & Howell, S. H. (1986) *Science* 234, 856–859.
37. Kowalski, D., Koreker, W. D. & Laskowski, M. (1976) *Biochemistry* 15, 4457–4467.
38. Carlson, P. S. (1973) *Proc. Natl. Acad. Sci. USA* 70, 598–602.
39. Bonnett, H. T. & Eriksson, T. (1974) *Planta* 120, 71–79.
40. Bonnett, H. T. (1976) *Planta* 131, 229–233.

Variations on the above embodiments are readily within the skill of the ordinary artisan and do not depart from the scope of the present invention, as described in the following claims.

What is claimed is:

1. A method of transforming a plant etioplast comprising:
    (a) providing a cell-free suspension of etioplasts;
    (b) treating said etioplast suspension with a metal chelating agent whereby any etioplast nuclease activity is diminished to provide a suspension of nuclease-inactivated etioplasts; and
    (c) incubating said suspension of nuclease-inactivated etioplasts with foreign DNA molecules in the presence of ethylene diamine-tetraacetic acid (EDTA) under conditions which provide for the uptake of said foreign DNA molecules into said etioplasts, wherein said foreign DNA molecules comprise an expression cassette, whereby transformed etioplasts are obtained.

2. A method for transforming isolated etioplasts into a stably transformed chloroplast which comprises incubating a suspension of an etioplast whose nuclease is inactivated by a chelating agent, with an expression cassette which comprises exogenous DNA comprising a coding sequence, control sequences comprising a promoter functional in chloroplast and a transcription terminator sequence functional in chloroplast, and chloroplast DNA flanking the expression cassette, to facilitate stable integration of the DNA with chloroplast DNA making up the genome of the cell by homologous recombination, whereby the DNA is stably integrated and inherited through organelle replication in daughter cells, allowing the foreign DNA to be taken up into the etioplast, and allowing the etioplast to mature and green into a stably transformed plant chloroplast.

3. The method of claim 2 in which the incubation of the suspension of nuclease-inactivated etioplast with foreign DNA is in the absence of ATP and of Mg and Ca cations.

4. The method of claim 2 wherein the chelating agent is EDTA.

5. The method of claim 2 wherein the coding sequence is a gene coding for herbicide resistance.

6. The method of claim 2 in which the expression cassette comprises a marker gene which encodes a selectable phenotype.

7. The method of claim 2 wherein the plant is selected from the group consisting of higher and lower plants.

8. The method of claim 7 wherein the higher plant is selected from the group consisting of dicotyledons and monocotyledons.

9. An isolated nuclease-inactivated etioplast which comprises foreign DNA, wherein said nuclease inactivation is due to incubation with a chelating agent.

10. The etioplast of claim 9 in which the foreign DNA comprises an expression cassette, which comprises control sequences.

11. The etioplast of claim 10 in which the control sequences comprise a promoter functional in chloroplast, a transcription termination and a marker gene.

12. The etioplast of claim 11 wherein the expression cassette comprises a coding sequence and control sequences, and the cassette is flanked by chloroplast DNA to facilitate stable integration of the expression cassette into the chloroplast genome by homologous recombination.

13. A transcription/translation active transformed chloroplast which comprises an expression cassette which comprises foreign DNA comprising a coding sequence, which chloroplast results from the maturing and greening of an isolated chelating agent-mediated nuclease inactivated etioplast, wherein the expression cassette is flanked by chloroplast DNA to facilitate stable integration of the expression cassette into the chloroplast genome by homologous recombination, whereby the DNA is stably integrated and inherited through organelle replication in daughter cells.

14. A transformed transcription/translation active chloroplast of a higher plant, which is competent for uptake of exogenous DNA which comprises an expression cassette comprising exogenous DNA comprising a coding sequence, control sequences which comprise a chloroplast promoter, a chloroplast origin of replication and a transcription termination sequence functional in chloroplast, whereby there is provided expression of the coding sequence in the chloroplast.

15. The transformed transcription/translation active chloroplast of claim 14 wherein the chloroplast promoter is selected from the psbA, the RbcL and the atpB promoters.

16. The transformed transcription/translation active chloroplast of claim 14 wherein the expression cassette comprises a selectable marker gene which encodes a selectable phenotype.

17. The transformed transcription/translation active chloroplast of claim 16 wherein the marker gene is the gene for chloramphenicol acetyltransferase, neomycin phosphotransferase II, nopaline synthase, dihydrofolate reductase, hypoxanthine phosphoribosyl transferase, or thymidine kinase.

18. The transformed transcription/translation active chloroplast of claim 14 wherein the coding sequence comprises the atrazine resistant gene psbA, the glyphosphate resistant gene ESPS synthase or a mutant of the gene for ribulose bisphosphate carboxylate/oxygenase (RuBisCO).

19. A stably transformed transcription/translation active chloroplast of a higher plant, which is competent for uptake of exogenous DNA, which comprises an expression cassette comprising exogenous DNA comprising a coding sequence, control sequences which comprise a promoter functional in chloroplast and a transcription termination sequence functional in chloroplast, whereby there is provided expression of the coding sequence in the chloroplast, and chloroplast DNA flanking the expression cassette to facilitate stable integration of the DNA with chloroplast DNA making up the genome of the cell by homologous recombination, whereby the DNA is stably integrated and inherited through organelle replication in daughter cells.

20. The transformed transcription/translation active chloroplast of claim 19 wherein the flanking DNA is chloroplast DNA and the promoter function in chloroplast is a chloroplast promoter.

21. The transformed transcription/translation active chloroplast of claim 20 wherein the chloroplast promoter is selected from the psbA, the rbcL and the atpB promoters.

22. The transformed transcription/translation active chloroplast of claim 19 wherein the expression cassette comprises a selectable marker gene which encodes a selectable phenotype.

23. The transformed transcription/translation active chloroplast of claim 22 wherein the selectable marker gene is the gene for chloramphenicol acetyltransferase, neomycin phosphotransferase (neo$^R$), neomycin phosphotransferase II, nopaline synthase, dihydrofolate reductase, hypoxanthine phosphoribosyl transferase, or thymidine kinase.

24. The transformed transcription/translation active chloroplast of claim 19 wherein the coding sequence comprises the atrazine resistant psbA gene, the glyphosate resistant ESPS synthase gene or a mutant of the gene for ribulose bisphosphate carboxylate/oxygenase (RuBisCo) which promotes catalytic activity.

25. An expression cassette for stably transforming chloroplast of higher plants comprising exogenous DNA comprising a coding sequence, control sequences comprising a promoter functional in chloroplast and a transcription terminator sequence functional in chloroplast, and chloroplast DNA sequences flanking the expression cassette to facilitate stable integration of the DNA with chloroplast DNA making up the genome of the cell by homologous recombination, whereby the DNA is stably integrated and inherited through organelle replication in daughter cells.

26. The expression cassette of claim 25 wherein the flanking DNA is the chloroplast DNA and the promoter functional in chloroplast is a chloroplast promoter.

27. The expression cassette of claim 26 wherein the promoter is selected from the psbA, the rbcL and the atpB promoters.

28. The expression cassette of claim 25 which comprises a selectable marker gene which encodes a selectable phenotype.

29. The expression cassette of claim 28 wherein the selectable marker gene is the gene for chloramphenicol acetyltransferase, neomycin phosphotransferase (neo$^R$), neomycin phosphotransferase II, nopaline synthase, dihydrofolate reductase, hypoxanthine phosphoribosyl transferase, or thymidine kinase.

30. The expression cassette of claim 25 wherein the coding sequence comprises the atrazine resistant psbA gene, the glyphosate resistant ESPS synthase gene or a mutant for the gene for ribulose bisphosphate carboxylate/oxygenase (RuBisCo).

31. The expression cassette of claim 25 wherein the cassette is flanked by restriction sites to facilitate cloning.

32. The transformed transcription/translation active chloroplast of claim 24 wherein the coding sequence comprises the glyphosate resistant gene ESPS synthase gene.

33. The expression cassette of claim 30 wherein the coding sequence comprises the glyphosate resistant ESPS synthase gene.

34. A cloning vector which comprises the expression cassette of claim 25.

35. The transformed transcription/translation active chloroplast of claim 24 wherein the coding sequence comprises the atrazine resistant psbA gene.

36. The expression cassette of claim 30 wherein the coding sequence comprises the atrazine resistant psbA gene.

37. The transformed chloroplast of claim 24 which is a monocotyledonous or dicotyledonous chloroplast.

38. The transformed chloroplast of claim 37 wherein the monocotyledonous chloroplast is that of wheat, corn, barley or rice.

39. The transformed chloroplast of claim 37 wherein the dicotyledonous chloroplast is that of peas, lentils, watermelon, sunflower, soybeans or cucumbers.

40. An expression vector which comprises control sequences comprising a chloroplast promoter functional in chloroplast, a transcription termination sequence whereby there is provided expression of a coding sequence in a plant chloroplast and downstream of the promoter, a restriction site for cloning the coding sequence.

41. The expression vector of claim 40 which also comprises a coding sequence inserted in the restriction site.

42. The expression vector of claim 41 wherein the coding sequence is a gene selected from the group consisting of EPSPS and psbA genes.

* * * * *